(12) United States Patent
Kiel et al.

(10) Patent No.: US 8,012,506 B2
(45) Date of Patent: *Sep. 6, 2011

(54) TANNATE COMPOSITIONS, METHODS OF MAKING AND METHODS OF USE

(75) Inventors: Jeffrey S. Kiel, Gainesville, GA (US); H. Greg Thomas, Carrollton, GA (US); Narasimhan Mani, Port Jefferson, NY (US)

(73) Assignee: Pernix Therapeutics, LLC, Gonzales, LA (US)

( * ) Notice: Subject to any disclaimer, the term of this patent is extended or adjusted under 35 U.S.C. 154(b) by 1277 days.

This patent is subject to a terminal disclaimer.

(21) Appl. No.: 11/501,649

(22) Filed: Aug. 9, 2006

(65) Prior Publication Data

US 2007/0020332 A1    Jan. 25, 2007

Related U.S. Application Data

(63) Continuation-in-part of application No. 10/921,438, filed on Aug. 19, 2004, now Pat. No. 7,094,429, which is a continuation of application No. 10/119,285, filed on Apr. 9, 2002, now Pat. No. 6,869,618, application No. 11/501,649, which is a continuation-in-part of application No. 10/269,027, filed on Oct. 10, 2002, now Pat. No. 7,273,623.

(60) Provisional application No. 60/282,969, filed on Apr. 10, 2001, provisional application No. 60/328,990, filed on Oct. 12, 2001.

(51) Int. Cl.
*A16K 9/14* (2006.01)
*A01N 33/02* (2006.01)
*A01N 43/40* (2006.01)

(52) U.S. Cl. ........ 424/489; 514/849; 514/850; 514/853; 514/937; 514/653

(58) Field of Classification Search ........................ None
See application file for complete search history.

(56) References Cited

U.S. PATENT DOCUMENTS

| | | | |
|---|---|---|---|
| 5,663,415 A * | 9/1997 | Chopdekar et al. ............. 560/68 |
| 6,287,597 B1 * | 9/2001 | Gordziel ...................... 424/464 |
| 6,340,695 B1 | 1/2002 | Gervais |
| 6,509,492 B1 | 1/2003 | Venkatamaran |
| 6,790,980 B1 | 9/2004 | Venkatamaran |
| 6,869,618 B2 | 3/2005 | Kiel et al. |
| 7,094,429 B2 | 8/2006 | Kiel et al. |
| 2003/0077321 A1 | 4/2003 | Kiel et al. |
| 2004/0157784 A1 | 8/2004 | Chopdekar |
| 2004/0234593 A1 | 11/2004 | Kiel et al. |
| 2004/0259809 A1 | 12/2004 | Gonzales |
| 2005/0037979 A1 | 2/2005 | Ping |
| 2005/0053656 A1 | 3/2005 | Ping |
| 2005/0069584 A1 | 3/2005 | Kiel et al. |
| 2005/0069585 A1 | 3/2005 | Kiel et al. |
| 2005/0202050 A1 | 9/2005 | Kiel et al. |
| 2005/0202080 A1 | 9/2005 | Kiel et al. |
| 2005/0232986 A1 | 10/2005 | Brown et al. |
| 2005/0232987 A1 | 10/2005 | Srinivason et al. |
| 2005/0232993 A1 | 10/2005 | Brown et al. |
| 2005/0281875 A1 | 12/2005 | Srinivason et al. |
| 2006/0057205 A1 | 3/2006 | Srinivason et al. |
| 2006/0269597 A1 | 11/2006 | Ping |
| 2006/0269598 A1 | 11/2006 | Ping |

* cited by examiner

*Primary Examiner* — Robert A Wax
*Assistant Examiner* — Jeffrey Palenik
(74) *Attorney, Agent, or Firm* — Jones Walker

(57) ABSTRACT

Tannate compositions containing active pharmaceutical ingredients to be used for treating nausea, vomiting, pain, convulsions, and insomnia and manufacturing processes for preparing the tannate compositions.

14 Claims, No Drawings

TANNATE COMPOSITIONS, METHODS OF MAKING AND METHODS OF USE

This is a continuation-in-part of U.S. patent application Ser. No. 10/921,438 filed on Aug. 19, 2004 now U.S. Pat. No. 7,094,429 which is a continuation of Ser. No. 10/119,285, filed Apr. 9, 2002, now U.S. Pat. No. 6,869,618 which claims the benefit of U.S. Provisional Patent Application Ser. No. 60/282,969 filed Apr. 10, 2001; and U.S. patent application Ser. No. 10/269,027 filed Oct. 10, 2002 now U.S. Pat. No. 7,273,623 which claims the benefit of U.S. Provisional Patent Application Ser. No. 60/328,990 filed Oct. 12, 2001.

FIELD OF THE INVENTION

The invention relates to tannate compositions containing active pharmaceutical ingredients selected from the following therapeutic classes: antinausea, antiemetic, antiinsomnia, analgesics and anticonvulsives. The invention also relates to methods of making the above tannate compositions and methods of use.

BACKGROUND OF THE INVENTION

The use of tannate salts of active pharmaceutical ingredients is well known. U.S. Pat. No. 6,287,597 describes tannate products containing pyrilamine tannate and phenylephrine tannate. The January 1990 issue of *Annals of Allergy*, Volume 64, describes combinations of chlorpheniramine tannate, pyrilamine tannate and phenylephrine tannate. An article in *Clinical Medicine*, dated September 1965, pages 1475-1478, describes tablets of pyrilamine tannate, chlorpheniramine tannate and amphetamine tannate. Phenylephrine tannate compositions are disclosed in U.S. Pat. No. 5,599,846 and phenylephrine tannate and chlorpheniramine tannate compositions are disclosed in U.S. Pat. No. 6,037,358. None of these references describe the problems with tannate pharmaceutical products caused by the large size of the tannate molecule. Because of its size, the percentage of active free base within the tannate salt is significantly lower than that in other salt forms such as the hydrochloride or maleate. The presence of low active percentages and the variable purity of the commercially available tannate salts leads to the stoichiometry of the active free base to tannic acid in the tannate salts to vary from batch to batch. This problem was noted in U.S. Pat. Nos. 5,599,846 and 5,663,415. This causes significant processing problems during manufacture and increases the likelihood that commercially available pharmaceutical products contain variable and in some instances, sub-therapeutic levels of the active drug substances creating dosing problems. None of these references suggest or describe pharmaceutical compositions containing tannate salts of active ingredients that are prepared with reduced variability in active drug content and increased certainty that the active drug is delivered within the therapeutic range. Also, none of the references suggest or describe tannate pharmaceutical compositions in the therapeutic classes of active ingredients for antinausea, antiemetic, antiinsomnia analgesics, or anticonvulsives.

None of the references discussed above suggest or describe the production of a tannate composition by means of an in-situ conversion of the active ingredient to the tannate salt in the presence of a dispersing agent using the method described herein to provide a dosage form which affords a sustained release of the active ingredient over prolonged intervals of time. Since the prolonged drug release character of the tannate salt enables the development of less frequent dosing regimens, such a composition is needed to improve patient compliance with dosage requirements.

SUMMARY OF THE INVENTION

The present invention relates to therapeutic compositions for symptomatic treatment of nausea, vomiting, insomnia, pain and convulsions in a warm-blooded animal where that composition comprises a pharmaceutically effective amount of an active pharmaceutical ingredient in each category as a tannate of consistent purity.

The present invention also relates to therapeutic compositions comprising a pharmaceutically effective amount of representative active pharmaceutical ingredients as tannates for each of the above therapeutic categories combined with non-tannate forms of the active pharmaceutical ingredient to provide both immediate and sustained release characteristics in the same dosage form.

The above therapeutic compositions are incorporated into various dosage forms such as semi-solid dosage forms which include liquid suspensions and soft gelatin capsules and solid dosage forms which include capsules, chewable tablets, and tablets.

The present invention also relates to a manufacturing process for in-situ conversion and incorporation thereof, of tannate salt complexes of antinausea, antiemetic, antiinsomnia, analgesic and anticonvulsive classes of pharmaceutical compounds into a sustained release therapeutic dosage form. By starting with a commonly available salt or free base of the active pharmaceutical ingredient, which is subsequently converted and incorporated in-situ as a tannate salt complex, the invention provides an efficient and reproducible method of manufacture for both solid and liquid or semi-solid products containing active ingredient tannate salt complexes.

The manufacture of tannate liquid and semi-solid dosage forms is performed according to processes described in U.S. Pat. No. 6,869,618 and U.S. Pub. No. 2005/0202050, both references are incorporated herein by reference.

The manufacture of tannate solid dosage forms is performed according to U.S. Pub. No. 2003/0077321 and U.S. Pub. No. 2005/0202080, both references are incorporated herein by reference.

The present invention also relates to methods of administering a pharmaceutically effective amount of active ingredient tannate complex of consistent purity to a warm-blooded animal.

DETAILED DESCRIPTION OF THE INVENTION

The present invention relates to a novel therapeutic composition containing a tannate salt of active ingredients of consistent purity selected from the antinausea therapeutic class. A representative active ingredient is doxylamine prepared by a tannate conversion process which includes the steps of mixing the doxylamine as a salt or in the free base form with tannic acid in a suitable solvent to generate a mixture. The mixing step is performed in the presence of a dispersing agent such as magnesium aluminum sulfate either natural or synthetic, preferably synthetic. The presence of the dispersing agent prevents the clumping and aggregation of the tannate salt formed and promotes uniformity in the mixture. Example 1, which is illustrative of a typical suspension formulation of the present invention, is prepared as follows:

Example 1

Preparation of Doxylamine Tannate Suspension

| Ingredient | % W/V | Amount (Kg) |
|---|---|---|
| Doxylamine Succinate | 0.100% | 1.7 |
| Tannic Acid | 0.325% | 5.525* |
| Neusilin ™, UFL2 | 0.800% | 13.600 |
| Xanthan Gum | 0.350% | 5.950 |
| Sodium Citrate Dihydrate | 1.000% | 17.000 |
| Citric Acid | 0.200% | 3.4 |
| Glycerin | 20.000% | 340.000 |
| Saccharin Sodium | 0.400% | 6.800 |
| Methylparaben | 0.200% | 3.400 |
| Sodium Benzoate | 0.100% | 1.700 |
| Sucrose | 10.000% | 170.000 |
| Artificial Bubble Gum Flavor PFC9861 | 1.100% | 18.700 |
| FD&C Blue #1 | 0.010% | 0.170 |

* = Based on 100% pure, anhydrous material

Purified water, 1200 kg, is added to a 500 gallon mixing vessel. Sodium citrate dihydrate and citric acid are added to the purified water and are mixed until dissolved. The neusilin and xanthan gum are added and thoroughly dispersed. Then the tannic acid is added and thoroughly dispersed. The doxylamine succinate is then added and mixing is continued for 20-30 minutes. The sucrose and saccharin sodium are added and dispersed. The artificial bubble gum flavor and FD&C Blue #1 are added and mixed for approximately 5 minutes. After adding and dispersing the glycerin, methylparaben and sodium benzoate, the pH of the formulation is adjusted to within the range of 4.8-5.2 and the suspension is diluted to a final volume of 1700 L and mixed for 30 minutes.

Example 2

Preparation of Doxylamine Tannate Soft Gel Capsule

| Ingredient | % In Total W/V | Amount (g) |
|---|---|---|
| Doxylamine Succinate | 26.67 | 400.00 |
| Tannic Acid, USP | 40.00 | 600.00 |
| Magnesium Aluminum Silicate | 6.67 | 100.00 |
| Lactose | 20.0 | 300.00 |
| Purified Water, USP | 6.67 | 100.00 |
| Totals | 100.00 | 1500.00 |

The tannic acid, doxylamine succinate, magnesium aluminum silicate and lactose powders were mixed for a period of 10 minutes in a planetary mixer to obtain a uniform blend. While continuing to mix, 150 mL of purified water was sprayed onto the dry powder blend. The conversion process occurred as soon as the tannic acid and API salts were moistened. Mixing was continued for an additional 20 minutes. At this point, the conversion product had a dough-like consistency, but was still able to be poured from the bowl. The wet mass material was incorporated into soft gelatin capsules using techniques known in the art.

A non-exclusive list of other antinausea therapeutic agents that can be used in the above Examples are: prochlorperazine, promethazine HCl, metochlopromide HCl, trimethobenzamide HCl, and ondansetron HCl.

Example 3

Preparation of Promethazine Tannate Suspension

| Raw Material | % in total | Total weight Reqd. (g) |
|---|---|---|
| Promethazine HCl, USP | 0.50% | 50.000 |
| Tannic Acid, USP | 0.50% | 50.000 |
| Neusilin Grade UFL2 | 0.80% | 80.0000 |
| Sodium Citrate Dihydrate, USP | 1.90% | 190.0000 |
| Aspartame | 0.20% | 20.0000 |
| Acesulfame K | 0.20% | 20.0000 |
| Glycerin, USP | 20.00% | 2000.0000 |
| Citric Acid, Anhydrous, USP | 1.15% | 115.0000 |
| Methylparaben, NF | 0.20% | 20.0000 |
| Sodium Benzoate, NF | 0.10% | 10.0000 |
| Xanthan Gum | 0.45% | 45.0000 |
| Strawberry Flavor | 0.40% | 40.0000 |
| FD&C Red #40 | 0.040% | 4.0000 |
| Purified Water, USP | 74.06% | 7406.0000 |
| Total | 100.00% | 10000.0 |

Promethazine HCl is dissolved in purified water. In a stainless steel mixing tank, the neusilin and tannic acid are dispersed in water using a suitable stirrer. While stirring the neusilin/tannic acid dispersion in the tank at low speed, the promethazine HCl solution is transferred in small portions to the dispersion. Stirring is continued for a minimum of 10 minutes.

In a separate mixing tank, the citric acid and sodium citrate are dissolved in purified water. The xanthan gum is slowly added and mixed until dispersed. The contents of the tank containing the active ingredient/tannic acid conversion are transferred to the xanthan gum suspending medium and mixed for a period of 10-30 minutes. The sweeteners, colors and flavors are subsequently added to the suspending medium with mixing. The sodium benzoate and methylparaben are dispersed in glycerin and subsequently added to the suspending medium and mixed to achieve a uniform dispersion. The pH is adjusted to pH 5 and purified water is added to the required volume.

A non-exclusive list of other antiemetic therapeutic agents that can be used in the above Example are: cyclizine, diphenhydramine, meclizine, chlorpromazine, droperidol, hydroxyzine, metoclopramide, prochlorperazine, and trimethobenzamide, cisapride, h2-receptor antagonists, and ondansetron.

Example 4

Preparation of Hydrocodone Tannate Tablet Dosage Form

| Raw Material | % W/W | Total wt. (kg) |
|---|---|---|
| Hydrocodone Bitartrate | 0.5 | 0.250 |
| Tannic Acid, USP | 0.5 | 0.250 |
| Magnesium Aluminum Silicate, NF | 8.12 | 4.060 |
| Avicel PH 102 | 67.76 | 33.880 |
| Methocel E-10M | 1.40 | 0.700 |
| Corn Starch | 0.80 | 0.400 |
| Di-Pac | 12.00 | 6.000 |
| Sodium Saccharin | 2.00 | 1.000 |
| Calcium Phosphate Dibasic | 2.80 | 1.400 |
| Xanthum Gum | 3.00 | 1.500 |
| Talc | 0.56 | 0.280 |

-continued

Preparation of Hydrocodone Tannate Tablet Dosage Form

| Raw Material | % W/W | Total wt. (kg) |
|---|---|---|
| Magnesium Stearate | 0.56 | 0.280 |
| Purified Water | N/A | 8.5 L* |
| Total | 100.000% | |

*Removed upon drying

Add the hydrocodone bitartrate, tannic acid, magnesium aluminum silicate, avicel pH102 and methocel E-10M to a small paddle blender. While mixing the powders, spray with purified water. The material should exhibit a dough-like texture when complete. Add the remaining powders and mix until uniform. If excess water is present, it may be removed by drying prior to tabletting using conventional techniques.

A non-exclusive list of other analgesics that can be used in the above Example are: codeine, diacetylmorphine, dihydrocodeine, hydromorphone, meperidine, methadone, morphine, oxycodone, oxymorphone and propoxyphene.

Example 5

Preparation of Diazepam Tannate Suspension

| Raw Material | % W/V | mg/5 ml |
|---|---|---|
| Diazepam | 0.100% | 5 |
| Tannic Acid | 0.100% | 5 |
| Saccharin Sodium | 0.300% | 0.015 |
| Sucrose | 10.000% | 0.500 |
| Glycerin | 7.500% | 0.375 |
| Magnesium Aluminum Silicate | 0.800% | 0.040 |
| Xanthum gum | 0.520% | 0.026 |
| Dibasic sodium phosphate | 1.000% | 1.050 |
| Methylparaben | 0.200% | 0.010 |
| Sodium benzoate | 0.100% | 0.005 |
| FD&C Red No. 40 | 0.040% | 0.002 |
| Strawberry Flavor | 0.500% | 0.025 |
| Purified Water | qs to volume | N/A |

The sodium phosphate dibasic is dissolved in purified water in a suitable stainless steel mixing tank. The MAS, followed by xanthan gum, is dispersed in the solution. The coloring agent FD&C Red No. 40 and the artificial strawberry flavor are then added and mixed to generate the suspending medium. In a separate mixing tank, the MAS and tannic acid are dispersed in water using a suitable stirrer. Mixing is continued until a uniform dispersion is achieved.

Diazepam is dissolved in purified water. While stirring the MAS/tannic acid dispersion in the mixing tank at low speed, the diazepam solution is transferred in small portions to the dispersion. Stirring is continued for a minimum of 10 minutes. After mixing, the contents of the tank are transferred to the suspending medium and mixed for a period of 5 minutes.

The sodium benzoate and methylparaben are dispersed in glycerin in a mixing tank using a suitable mixer. The glycerin mixture is then added to the suspending medium and mixed to achieve a uniform dispersion. Finally, purified water is added to make up the suspension to the required volume.

A non-exclusive list of other sedatives that can be used in the above Example are: clorazepate, estazolam, flurazepam, lorazepam, midazolam, nitrazepam, oxazepam, temazepam, triazolam, quazepam, zolpidem, zaleplon, amitriptyline, trimipramine, and trazodone.

Example 6

Preparation of Phenytoin Tannate Chewable Tablet

| Ingredient | % W/V | Amount (Kg) |
|---|---|---|
| Phenytoin | 10.00 | 4.840 |
| Tannic Acid, USP | 10.00 | 4.840 |
| Neusilin | 1.35 | 0.653 |
| Mannitol | 35.50 | 17.180 |
| Sodium Saccharin | 0.90 | 0.396 |
| Corn Starch | 0.90 | 0.446 |
| Methocel E-10M | 1.35 | 0.653 |
| DiPac | 48.83 | 21.500 |
| Calcium Phosphate Dibasic | 2.70 | 1.188 |
| Xanthan Gum | 1.57 | 0.691 |
| Artificial Strawberry Flavor | 0.90 | 0.396 |
| FD&C Blue No. 1 | 0.09 | 0.040 |
| Talc | 0.45 | 0.198 |
| Magnesium Stearate | 0.45 | 0.198 |
| Purified Water | NA | NA |

The tannic acid and neusilin powders are mixed in a blender for about 10 minutes. The phenytoin is dissolved in water and sprayed onto the powders while mixing. The mannitol and sodium saccharin are added and mixed until uniform. The methocel is added and mixed until uniform. An aqueous solution of corn starch is then applied to the powders while mixing.

After drying to remove the excess water, the material is milled. The milled powder is then blended with the remaining ingredients dipac, calcium phosphate dibasic, xanthan gum, flavor, color, magnesium stearate and talc until uniform and compressed into tablets using techniques known in the art.

A non-exclusive list of other anticonvulsion therapeutic agents that can be used in the above Example are: hydantoins including mephenytoin; succimides including ethosuximide and methsuccimide; benzodiazepines, which are better known for their use as tranquilizers and sedatives, including clonazepam, clorazepate, diazepam, carbamazepine, valproic acid, gabapentin, topiramate, felbamate, and phenobarbital.

Example 7

Preparation of Dimenhydrinate Tannate and Dimenhydrinate Non-Tannate Tablet Dosage Form

| Ingredient | % In Total, w/v | Amount (g) |
|---|---|---|
| Dimenhydrinate | 12.50% | 1000.0 |
| Tannic Acid, USP | 12.50% | 750.00 |
| Magnesium Aluminum Silicate (MAS), NF | 2.00% | 176.00 |
| Methocel E-10M (HPMC) | 35.88% | 3157.42 |
| Lactose | 32.53% | 2602.58 |
| FD&C Blue #1 Aluminum Lake | 0.30% | 24.00 |
| Colloidal Silicon Dioxide | 0.50% | 40.00 |
| Magnesium Stearate, NF | 1.25% | 100.00 |
| Purified Water, USP~* | NA | 150.00 |
| TOTAL | 100.00% | 8000.0 |

*An excess of 10% is added to raw materials used in the wet granulation to correct for losses.

Tablets utilizing the above formulation are prepared as follows. The tannic acid, MAS, and ¾ dimenhydrinate dry powders are mixed for a period of 10 minutes in a planetary mixer to obtain a uniform blend. While continuing to mix, 150 mL of purified water is sprayed onto the dry powder blend. The conversion process occurs as soon as the tannic acid and API salts are moistened. Mixing is continued for an additional 20 minutes. At this point, the conversion product has a dough-like consistency, but is still able to be poured from the bowl.

To a separate mixing vessel, most preferably a paddle blender, the following dry powders are added: methocel E-10M (HPMC) and lactose. The conversion product is poured evenly over these dry powders, and the mixture is then blended for 20 minutes. At this point, a product resembling a typical wet granulation is obtained. The mixture is then dried and milled as needed. The remainder of the excipients and the dimenhydrinate are added and the mixture is blended for an additional 20 minutes. The final blend is then processed into tablets using techniques well known in the art.

Reasonable variations, such as those which would occur to a skilled artisan, can be made herein without departing from the scope of the invention.

The invention claimed is:

1. A process for the conversion of at least one active pharmaceutical ingredient into a tannate salt complex for incorporation into a therapeutic liquid or semi-solid dosage form, the process comprising the steps of:
   (a) dissolving the salt or free base of the active pharmaceutical ingredient in a pharmaceutically acceptable liquid in the presence of a dispersing agent and tannic acid under stirring, to form a dispersion wherein the tannic acid component is of either a natural or synthetic source;
   (b) combining the tannate salt complex of the active pharmaceutical ingredient without isolation or purification with pharmaceutically acceptable excipients to generate a therapeutic dosage form.

2. The process according to claim 1 wherein the dispersing agent provided in step (a) is selected from the group consisting of natural magnesium aluminum silicate and synthetic magnesium aluminum silicate.

3. The process according to claim 2 wherein the dispersing agent is synthetic magnesium aluminum silicate.

4. The process according to claim 1 wherein step (b) includes adding a non-tannate active pharmaceutical ingredient.

5. The process of claim 1 wherein the at least one active pharmaceutical ingredient is selected from the group consisting of an antinausea agent, antiemetic, sedative, analgesic and anticonvulsive.

6. The process of claim 5 wherein the analgesic is selected from the group consisting of: codeine, diacetylmorphine, dihydrocodeine, hydrocodone, hydromorphone, meperidine, methadone, morphine, oxycodone, oxymorphone and propoxyphene.

7. A process for the conversion of at least one active pharmaceutical ingredient into a tannate salt complex for incorporation into a therapeutic solid dosage form, the process comprising mixing the salt or free base of the at least one active pharmaceutical ingredient, tannic acid, and a dispersing agent in a pharmaceutically acceptable liquid to form a tannate salt complex of the at least one pharmaceutical active ingredient for incorporating into said therapeutic solid dosage form.

8. The process of claim 7 further comprising incorporating the tannate salt complex of the at least one pharmaceutical active ingredient into said therapeutic solid dosage form.

9. The process according to claim 7 wherein the dispersing agent is selected from the group consisting of natural magnesium aluminum silicate and synthetic magnesium aluminum silicate.

10. The process according to claim 7 wherein the dispersing agent is synthetic magnesium aluminum silicate.

11. The process according to claim 7 further comprising adding a non-tannate active pharmaceutical ingredient.

12. The process according to claim 7 wherein the at least one pharmaceutical active ingredient is selected from the group consisting of an antinausea agent, antiemetic, sedative, analgesic and anticonvulsive.

13. The process according to claim 12 wherein the analgesic is selected from the group consisting of: codeine, diacetylmorphine, dihydrocodeine, hydrocodone, hydromorphone, meperidine, methadone, morphine, oxycodone, oxymorphone and propoxyphene.

14. The process according to claim 8, wherein said therapeutic solid dosage form includes a tablet or a capsule.

* * * * *